United States Patent [19]

Gaur

[11] Patent Number: 5,088,993
[45] Date of Patent: Feb. 18, 1992

[54] SANITARY NAPKIN WITH INDIVIDUAL SELF WRAPPING MEANS

[75] Inventor: Umesh Gaur, North Brunswick, N.J.

[73] Assignee: McNeil-PPC, Inc., Milltown, N.J.

[21] Appl. No.: 617,460

[22] Filed: Nov. 21, 1990

Related U.S. Application Data

[63] Continuation of Ser. No. 238,372, Aug. 30, 1988, abandoned.

[51] Int. Cl.5 .............................................. A61F 13/15
[52] U.S. Cl. ................................. 604/385.1; 604/386; 206/438; 206/440
[58] Field of Search ................... 604/385.1, 386, 358; 206/438, 440

[56] References Cited

U.S. PATENT DOCUMENTS

| | | | |
|---|---|---|---|
| 3,626,945 | 7/1975 | Mobley | 128/289 |
| 3,963,029 | 6/1976 | Brooks | 604/385.1 |
| 3,973,567 | 8/1976 | Srinivasan et al. | 128/290 |
| 4,380,450 | 8/1982 | Reich | 604/386 |
| 4,605,403 | 8/1986 | Tucker | 604/385.1 |
| 4,735,316 | 4/1988 | Froidh | 206/440 |
| 4,917,675 | 4/1990 | Taylor et al. | 604/385.1 |
| 5,037,417 | 8/1991 | Ternstrom et al. | 604/385.2 |

Primary Examiner—Ronald Frinks
Assistant Examiner—K. M. Reichle

[57] ABSTRACT

A pre-wrapped sanitary napkin is disclosed having an elongated wrapping sheet that is extended around a folded portion of the napkin and adhered to itself to keep the napkin in a folded position using pressure-sensitive adhesive. This invention provides for individual wrapping of sanitary napkins without the added expense of an outer paper wrapper.

4 Claims, 1 Drawing Sheet

SANITARY NAPKIN WITH INDIVIDUAL SELF WRAPPING MEANS

This is a continuation of application Ser. No. 07/238,372, filed Aug. 30, 1988, now abandoned.

FIELD OF THE INVENTION

This invention relates to protective, absorbent liners for undergarments and their packaging, and more particularly, to napkins which are individually wrapped for cleanliness prior to use.

BACKGROUND OF THE INVENTION

Sanitary napkins have, in the past, been bundled with several napkins in a package which provided a means for keeping all the napkins clean, sanitary and undamaged. Unfortunately, this method left the napkins virtually unprotected from dirt and deforming pressures once a napkin was removed from the package and carried individually in a pocket or purse.

One innovative concept introduced in the marketplace to replace the multiple napkin package is the folding and individual packaging of sanitary napkins in a paper or plastic wrapping material. This method offers a discreet way of carrying sanitary napkins and also provides a more soil resistant product when individually carried in a purse. The outer wrap is customarily sealed around the napkin and can be easily taken off and discarded by the consumer at the time the napkin is used. Individually wrapping sanitary napkins, however, typically increases manufacturing costs associated with the requisite materials and processing of these wraps, and can ultimately result in an increased cost of the product.

Although not specifically addressing the problem of additional expense of a separate outside wrapper, Werner, U.S. Pat. No. 3,688,771, teaches a sanitary napkin that comprises free ends of a protective strip that extend around the extremities of the napkin and are folded over the top surface. Werner discloses that the free ends are used in this embodiment to cover and protect the body-contacting surface of the pad from inadvertent soilage before use. The protective strip of this device also serves as a means for covering the attachment adhesive means of the napkin. Werner suggests an alternative means for protecting a napkin. However, there is no teaching for the elimination of the outer wrap. This patent also fails to disclose the benefits of folding the napkin to provide a discreet way of carrying it before use. Moreover, since there is no teaching for fixing or adhering the free ends of Werner's product after folding them over the top surface of the napkin, the degree of cleanliness this product provides is questionable.

Accordingly, there is still a need for a napkin with wrapping means that provides for individual wrapping without added manufacturing and material costs. There is also a need for a less expensive napkin that can be discreetly stored until use. which is also resistant to contamination and deforming pressures.

SUMMARY OF THE INVENTION

A sanitary napkin is herein provided that is pre-wrapped for cleanliness prior to use without an additional outer paper wrapper. The napkin of this invention comprises an elongated wrapping sheet which extends beyond an end of the central absorbent element of the napkin to define a flap. The napkin is folded or rolled along its transverse axis such that portions of the body-facing side of the napkin's absorbent element are in contact with each other to form a folded portion. The flap of the elongated wrapping sheet is folded over the folded portion of the napkin and releasably adhered to an underlying portion of the wrapping sheet using pressure-sensitive adhesive. The underlying portion of the wrapping sheet may be coated with material which enables the release of the wrapping sheet, such as silicone. The adhesive may be located over the release coating or the release coating may extend only along the wrapping sheet as far as the area to be adhered to the adhesive. Accordingly, this napkin provides a more economical wrapping arrangement that also minimizes the amount of paper to be discarded, since the elongated wrapping sheet keeps the body-facing side relatively clean and also protects the attachment adhesive of the napkin. Moreover, this napkin can be inconspicuously hidden in a pocket, prior to use, since it is folded into a more manageable size.

In the more preferred embodiment of this invention, the sanitary napkin is folded twice across two transverse axes for an even more compact size Additionally, it is anticipated that the adhesive means for securing the flap to the elongated wrapping sheet may be located on the underlying portion of the wrapping sheet.

The sanitary napkin may also, in accordance with this invention be rolled around its transverse axis rather than being folded along discrete axes.

Also disclosed herein is a novel method for individually wrapping a folded, sanitary napkin. In this method, an elongated wrapping sheet is releasably adhered to a portion of the adhesive-bearing side of the napkin. The wrapping sheet is selected to have pressure-sensitive adhesive means for attaching a flap portion after the napkin is folded over onto its body-facing side. Also included herein, is a method of opening an individually wrapped and folded sanitary napkin. In this method, a napkin is provided with an elongated wrapping sheet having a flap which is folded over a folded portion of the napkin and releasably adhered to an underlying portion of the wrapping sheet by pressure-sensitive adhesive means. After stripping the flap away from the underlying portion of the wrapping sheet, the napkin can then be unfolded to expose its body-facing side. Finally, the wrapping sheet may be peeled away from the adhesive-bearing side of the absorbent element of the napkin and the napkin may then be attached to an undergarment.

It is, therefore, an object of this invention to provide a sanitary napkin that eliminates the manufacturing and material costs associated with an outer paper wrapping.

It is another object of this invention to provide a sanitary napkin that has less waste associated with its use.

It is still another object of this invention to provide a sanitary napkin that can be folded into a more compact size for more discreetly storing in a pocket or purse.

With these and other objects in view, which will become apparent to one skilled in the art as the description proceeds, this invention resides in the novel construction, combination, arrangement of parts and methods substantially as hereinafter described and more particularly defined by the attached claims.

BRIEF DESCRIPTION OF THE DRAWINGS

The accompanying drawings illustrate a complete embodiment of the invention according to the best mode so far devised for the practical application of the principles thereof, and in which.

DETAILED DESCRIPTION OF THE INVENTION

In accordance with the teaching of this invention, a pre-wrapped sanitary napkin is provided comprising an elongated absorbent element having a body-facing side and an adhesive-bearing side. Releasably adhered to at least a portion of the adhesive-bearing side of the absorbent element is an elongated wrapping sheet having pressure-sensitive adhesive means disposed thereon. The wrapping sheet extends beyond an end of the central absorbent element to define a flap. The napkin is packaged as a compact shape, being folded or rolled along at least one transverse axis, such that portions of the body-facing side of the absorbent element are in contact with each other to form a folded portion. The flap is folded over the folded portion of the napkin and adhered using adhesive means to an underlying portion of the wrapping sheet prior to use.

The napkin of this invention is individually wrapped by applying an elongated wrapping sheet to at least a portion of the adhesive-bearing side of the absorbent element of the napkin. The wrapping sheet is provided with pressure-sensitive adhesive means and is further selected to extend beyond an end of the central absorbent element to define a flap. Next, the napkin is folded along a transverse axis such that portions of the body-facing side of the absorbent element are in contact with each other to form a folded portion. Finally, the flap is wrapped around the folded portion of the napkin and releasably adhered to an underlying portion of the wrapping sheet to retain the napkin in a folded position prior to use.

Figure 1:
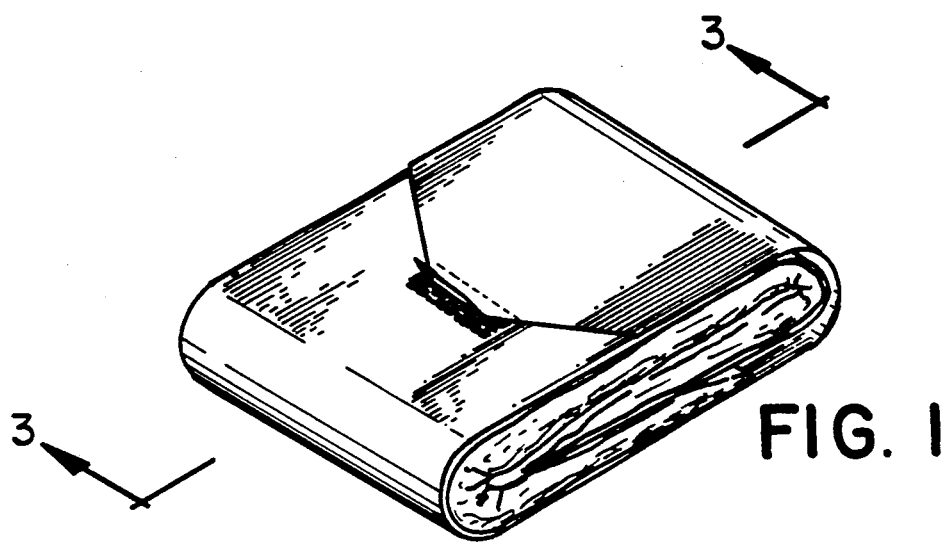
FIG. 1: Is a perspective view from the top of the napkin as it is packaged illustrating how the flap may be released from the adhesive means on the underlying wrapping member.
Figure 2:
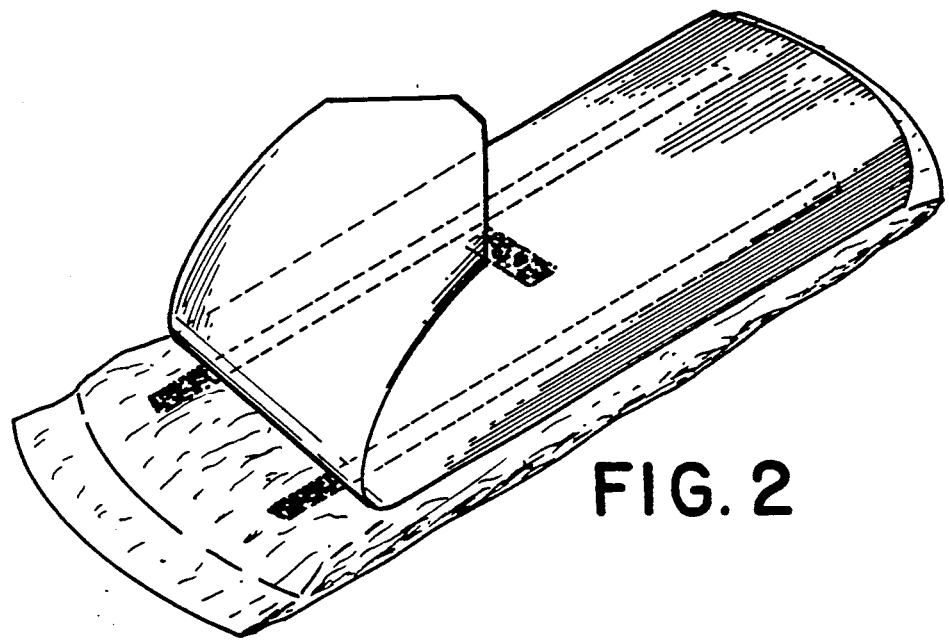
FIG. 2: Is a perspective view from the top of the napkin illustrating a fully extended product with a peel back view of the adhesive-bearing side of the napkin.
Figure 3:
FIG. 3: Is a detailed illustration of a longitudinal cross-sectional view of the napkin of FIG. 1, taken through line 3—3.

Referring now to FIGS. 1–3 which illustrate in perspective and cross-sectional views, a sanitary napkin 10 which is the subject of this invention. The napkin 10 comprises an elongated absorbent element 35 having a body-facing side and an adhesive-bearing side 12. An elongated wrapping sheet 40 is releasably adhered to at least a portion of the adhesive-bearing side 12 of the absorbent element 35. The wrapping sheet 40 has pressure-sensitive adhesive means 18 disposed thereon. The wrapping sheet also extends beyond an end 26 or 28 of the central absorbent element 35 to define a flap 15. As packaged, the napkin 10 is folded along at least one transverse axis, such that portions of the body-facing side of the absorbent element 35 are in contact with each other to form a folded portion 30. The flap 15 of this invention is folded over the folded portion 30 of napkin 10 as illustrated in FIG. 1 and secured to the underlying wrapper sheet 40.

The pressure-sensitive adhesive means 18 on the wrapping sheet 40 is disposed to releasably adhere the flap 15 to an underlying portion of the wrapping sheet 40 prior to use. It will be apparent to those skilled in the art that many different configurations for this invention can be prepared. For example, the adhesive means on the wrapping sheet may be in the form of a tape tab or strip extending from the end of flap 15 to secure the flap to the underlying wrapper. The attached FIGURES only represent a preferred embodiment of this invention and are not intended to limit the subject matter as claimed. The choice of materials for use in the napkin of this invention may be any of the well-known absorbent and super-absorbent materials utilized in the art of manufacturing these products. For example, the wrapping sheet may be either release-coated paper or a plastic film.

In a more preferred embodiment of this invention the adhesive means 18 is disposed on an underlying portion of the wrapping sheet 40 as described in FIG. 1. Additionally, it is preferred that the napkin is folded twice across two transverse axes of the napkin to form an even more compact size as illustrated in embodiment of FIG. 1. According to this invention, the flap 15 can be about the same width as the width of the elongated absorbent element 35, or narrower than the width of the absorbent element 35.

The method for individually wrapping a folded, sanitary napkin comprises providing an elongated absorbent element 35 having a body-facing side and an adhesive-bearing side 12. The method then directs that an elongated wrapping sheet 40 be applied to at least a portion of the adhesive-bearing side 12 of the absorbent element 35. This wrapping sheet 40 is provided with pressure-sensitive adhesive means 18 disposed thereon. The wrapping sheet 40 further is selected to extend beyond an end 26 or 28 of the elongated absorbent element 35 to define a flap 15. The method then directs that the napkin be folded along a transverse axis such that portions of the body-facing side of the absorbent element 35 are in contact with each other to form a folded portion 30 of the napkin, as illustrated in FIGS. 1 and 3. Finally, the flap 15 is wrapped around the folded portion 30 of the napkin. The adhesive means 18 on the wrapping sheet 40 is selected to releasably adhere the flap 15 to an underlying portion of the wrapping sheet 40 to retain the napkin in a folded position. Alternatively, the adhesive means may be applied directly to the underside of flap 15 which may then be secured to wrapping sheet as the napkin is folded. The folding step of this method can comprise folding the napkin across one or two transverse axes. Moreover, this method can comprise providing a wrapping sheet 40 having the same width as the width of the absorbent element 35, or a width that is narrower than the width of the absorbent element 35.

The elongated absorbent element 35 of this invention should be made of soft, comfortable material. Adequate absorbency may be built into the core of the absorbent 35 without adding bulk by adding super-absorbent materials, now known, which have the properties of high-liquid retention, e.g. cross-linked acrylate polymers. Generally, the absorbent element 35 should be about 4 to 10 inches in length, preferably about 6 to 9 inches.

As described in FIG. 3, the absorbent element 35 comprises a core 20 which preferably is made of loosely associated absorbent hydrophilic materials such as cellulose fibers, wood pulp, regenated cellulose or cotton fibers, and/or other materials generally known in the art. Such fibers may be chemically or physically modified and the core may include such fibers in combination with other materials, both natural and synthetic, such as hydrophilic foams, hydrophilic polymers and the like. For the preferred embodiment of this invention, wood pulp is the material of choice because of its availability and inexpensive costs.

As is customary in the art, a body fluid pervious surface 24 is provided as a covering on the side of the napkin to be worn against the body of the user. This surface may be a perforated film or any woven or non-woven material pervious to body fluid contacting its surface. The body-facing material should be soft and easily permeated by body fluids. Preferably, it should be a material which allows the passage of fluid while retaining little or no fluid in its structure to provide a relatively dry surface next to the skin. Generally, the fluid permeable surface 24 is a single, rectangular sheet of material having a width sufficient to cover the body-facing side of the absorbent element 35.

The sanitary napkin 10 of this invention further includes a body fluid impervious surface 22 on the garment-facing side of the absorbent element 35. The impervious surface 22 should perferably allow the passage of air and moisture vapor while substantially blocking the passage of fluid to the outer surface. The impervious surface 22 generally extends over the bottom surface and side edges of the absorbent element 35 and is sealed together with the pervious surface 24 around the perimeter of the absorbent element to prevent leakage of fluid from the sides of the absorbent element.

The impervious surface 22 may be heat sealed or fastened by way of adhesives to the core 20 or to the core 20 wrapped in a pervious surface cover. The impervious surface 22 may comprise any thin, flexible, body fluid impermeable material such as, a polymeric film, e.g., polyethylene, polypropylene, cellophane or even a normally fluid pervious material that has been treated to be impervious such as repellent paper or non-woven fabric. The fluid impervious surface 22 is generally fastened to the core 20 by means of a plurality of longitudinally extending lines of adhesive. Preferably, however, the impervious surface 22 is heat bondable material such as polyethylene which may be bonded to the pervious surface 24 to completely enclose the core 20.

An important aspect of this invention is the elongated wrapping sheet 40. Traditionally, the prior art has used release paper only to protect the adhesive means of the absorbent element 14 and 16. One important aspect of this invention is that the elongated wrapping sheet 40 not only protects the adhesive strips 14 and 16, but also may be adhered around a folded portion 30 of the napkin 10 to protect the body-facing side of the napkin 10 as depicted in FIG. 1. The elongated wrapping sheet 40 of this invention may be made of any suitable sheet-like material which adheres with sufficient tenacity to the adhesive means, i.e. strips 14 and 16, to remain in place, but which can be readily removed when the napkin 10 is to be used. Conventional materials used for this purpose include woven webs, non-woven bonded fiber webs, non-woven thread webs, thread reinforced non-woven webs, plastic films, i.e. polyethylene or polypropylene, and/or laminates of the above. A particularly useful material for this sheet 40 is a semi-bleached kraft paper, the adhesive contacting side of which has been silicone-coated to provide a releasable surface for easier removal from the adhesive 14 and 16 on the absorbent element 35.

The adhesive materials used for adhesive means 14, 16 and 18 may comprise any conventional pressure-sensitive adhesive material known in the art for use with sanitary napkins. As used herein, "pressure-sensitive adhesive" refers to any releasable adhesive material. Compositions suitable for sanitary napkins include, for example, the water-based pressure-sensitive adhesives such as the acrylate adhesives, e.g. vinyl acetate-2 ethyl hexyl acetate copolymer which is generally combined with tackifiers such as, for example, ethylene amine. Alternatively, the adhesive may comprise the rapid setting thermal plastic hot-melt adhesives. The adhesive elements may also comprise a two-sided adhesive tape. It is anticipated that adhesives based on an elostomer selected from natural or synthetic rubbers could also be used.

From the foregoing, it can be realized that this invention provides an improved sanitary napkin with a wrapping member that serves to protect the attachment adhesive strips of the absorbent element and also wraps around the absorbent element to protect the body-facing side of the napkin. This napkin features a more economical wrapping arrangement that eliminates the cost of adding a paper outer wrapping. Less waste is associated with this product since only the elongated wrapping sheet is disposed, as compared to disposing both the outer wrapper and a release paper strip of the more traditional napkins. Moreover, this product can be folded into a more compact size for discretely storing it in a pocket or purse. Although various embodiments have been illustrated, this was for the purpose of describing, but not limiting the invention. Various modification, which will become apparent to one skilled in the art, are within the scope of this invention described in the attached claims.

I claim:

1. A method for individually wrapping a folded, sanitary napkin comprising:
   (a) providing an elongated absorbent element having a body-facing side and an adhesive-bearing side;
   (b) applying an elongated wrapping sheet to at least a portion of said adhesive-bearing side of said absorbent element, said wrapping sheet being provided with pressure-sensitive adhesive means disposed thereon, said wrapping sheet further being selected to extend beyond an end of said elongated absorbent element to define a flap thereof;
   (c) folding said napkin along a transverse axis such that portions of said body-facing side of said absorbent element are in contact with each other to form a folded portion of said napkin; and
   (d) wrapping said flap around said folded portion of said napkin, said adhesive means on said wrapping sheet being selected to releasably adhere said flap to an underlying portion of said wrapping sheet to retain the napkin in a folded position prior to use.

2. The method claim 1, wherein said folding step comprises folding said napkin along two transverse axes of said napkin.

3. The method of claim 1, wherein said applying step comprises providing a wrapping sheet having the same width as the width of said absorbent element.

4. The method of claim 1, wherein said applying step comprises providing a flap having a narrower width than the width of said absorbent element.

* * * * *